(12) United States Patent
Ducharme (10) Patent No.: US 8,303,495 B2
(45) Date of Patent: Nov. 6, 2012

(54) MAGNETIC RETRACTION DEVICE

(75) Inventor: Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 221 days.

(21) Appl. No.: 12/648,750

(22) Filed: Dec. 29, 2009

(65) Prior Publication Data

US 2010/0168523 A1    Jul. 1, 2010

Related U.S. Application Data

(60) Provisional application No. 61/141,368, filed on Dec. 30, 2008.

(51) Int. Cl.
*A61B 1/32* (2006.01)
(52) U.S. Cl. .......... 600/207; 600/12
(58) Field of Classification Search .......... 600/12, 600/115, 116, 143, 206, 207, 208, 37; 606/191, 606/197–200, 203, 204, 206, 207, 208, 210, 606/215; 604/96.01–109; 623/1.11–1.12; 446/129, 137, 139
See application file for complete search history.

(56) References Cited

U.S. PATENT DOCUMENTS

| 7,163,506 | B2 | 1/2007 | Grise |
| 2007/0135685 | A1 | 6/2007 | Cuschieri |
| 2007/0244501 | A1 | 10/2007 | Horn |
| 2007/0270629 | A1* | 11/2007 | Charles .......... 600/12 |
| 2008/0108860 | A1* | 5/2008 | Bell et al. .......... 600/12 |
| 2008/0171907 | A1 | 7/2008 | Long et al. |

FOREIGN PATENT DOCUMENTS

| GB | 2 403 909 A | 1/2005 |
| WO | WO 00/66030 | 11/2000 |
| WO | WO 2008/067317 A2 | 6/2008 |
| WO | WO 2008/098166 A1 | 8/2008 |
| WO | WO 2008/101077 A1 | 8/2008 |

* cited by examiner

*Primary Examiner* — Kevin T Truong
*Assistant Examiner* — Diana S Jones
(74) *Attorney, Agent, or Firm* — Brinks Hofer Gilson & Lione (57) ABSTRACT

A magnetic retraction device is provided that may be used to manipulate organs and tissue. The device includes a magnetic agent, at least one inflatable member configured to contain the magnetic agent, and a magnetic device. The inflatable member can be disposed on an elongate member adapted for delivery into a patient lumen. The inflatable member can be interconnected with one or more additional inflatable members by a sling.

12 Claims, 8 Drawing Sheets

MAGNETIC RETRACTION DEVICE

PRIORITY CLAIM

The present disclosure claims the benefit of priority of U.S. Provisional Application Ser. No. 61/141,368, entitled "Magnetic Retraction Balloon," filed Dec. 30, 2008, the disclosure of which is hereby incorporated by reference in its entirety.

TECHNICAL FIELD

The present disclosure relates to medical devices, and more particularly, to medical devices for manipulating organs and tissue.

BACKGROUND

Surgeons have limited space with which to operate during minimally invasive surgery. In an effort to create more space, devices and techniques have been developed for the retraction and manipulation of organs and tissue adjacent to the surgical site. Current approaches include mechanical manipulation of the tissue, typically using clamps, paddles, graspers, and the like. However, organs and tissue can be damaged with these techniques by application of excessive force in the course of manipulation. In addition, mechanical instruments take up needed space at the surgical site and at the site of entry into the patient—often, an entire trocar is dedicated to retracting an organ in a laparoscopic procedure.

In order to avoid the difficulties presented by mechanical manipulation of organs and tissue, an iron-filling liquid may be injected into an organ and thereafter retracted magnetically. However, since the iron-filling material is generally considered non-biocompatible, simply injecting the material into desired organs is generally not clinically practical. Furthermore, making holes through organs by way of injection, especially those that secrete fluids such as the gall bladder, increases the risk of fluid leakage following the procedure.

Accordingly, what is needed are medical devices and methods where organs and tissue can be retracted without dependence on mechanical retraction instruments; where retraction can be achieved without dependence on T-anchors, sutures, and the like; where the endoscope is not dedicated to maintaining the retraction; where no magnetic fluid is in contact with the patient's body; and where the retraction is with a strong force, but is easily reversible.

SUMMARY

In one aspect, a system is provided for the manipulation of organs and tissue using a magnetic retraction device. In one embodiment, the system includes a magnetic agent, at least one inflatable member configured to contain the magnetic agent, and a magnetic device, wherein the magnetic device is configured to manipulate the position of the inflatable member containing the magnetic agent, wherein the inflatable member containing the magnetic agent is configured to manipulate the position of a target tissue or organ in response to a magnetic field emitted by the magnetic device. The system can include an elongate member having a distal portion, a proximal portion, and a lumen disposed through the proximal portion and at least partially through the distal portion, wherein the lumen is fluidly interconnected with the inflatable member. The elongate member can include a second lumen disposed through the proximal portion and the distal portion, wherein the second lumen is configured to receive a wire guide therethrough. The system can include a protective sheath or other similar device. The system can include a sling disposed on the distal portion of the elongate member. The system can include one or more expansion elements configured to radially expand the sling. The expansion elements may be self-expanding. The expansion elements can include a superelastic material such as, for example, nitinol. The sling can include a magnetic agent. The expansion elements can include one or more wires attached to the elongate member wherein the wires can be advanced longitudinally toward the distal end such that the sling radially expands upon advancement of the wires.

In another embodiment, the system can include a plurality of inflatable members configured to contain a magnetic agent, wherein the plurality of inflatable members are interconnected by a sling. The system can further include a magnetic agent and a magnetic device, wherein the magnetic device is configured to manipulate the position of the plurality of inflatable members containing the magnetic agent, wherein the plurality of inflatable members containing the magnetic agent are configured to manipulate the position of a target tissue or organ in response to a magnetic field emitted by the magnetic device. The sling may be self-expanding. The sling may include a superelastic material such as, for example, nitinol. The sling can include a magnetic agent. The system can include an elongate member having at least one lumen, the lumen fluidly interconnected with at least one of the plurality of inflatable members. Alternatively, at least one of the inflatable members can include a valve system adapted to detachedly connect to an inflation device.

In another aspect, a method is provided for the manipulation of organs and tissue. In one embodiment, the method includes introducing into a patient at least one inflatable member adapted to contain a magnetic agent; positioning the inflatable member so as to engage a target tissue or organ; introducing a magnetic agent into the inflatable member; and applying a magnetic field to the inflatable member containing the magnetic agent. The magnetic agent may be introduced into the inflatable member prior to introduction into the patient. Alternatively, the magnetic agent may be introduced during or after introduction into a patient. Optionally, the inflatable member may be disposed on an elongate member. In other embodiments, a plurality of inflatable members may be interconnected by a sling.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "tissue," as used herein, refers to all types of biological tissue, including organs and cells and parts thereof.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

Devices and Systems

One aspect of the present disclosure provides devices and systems for manipulating tissue and organs. The devices and systems can be of use in the retraction of organs and tissue during minimally invasive surgery. The devices and systems can be of particular use in retraction of organs during endoscopic or laparoscopic surgery, including for example, SILS (Single Incision Laparoscopic Surgery).

Figure 1A:
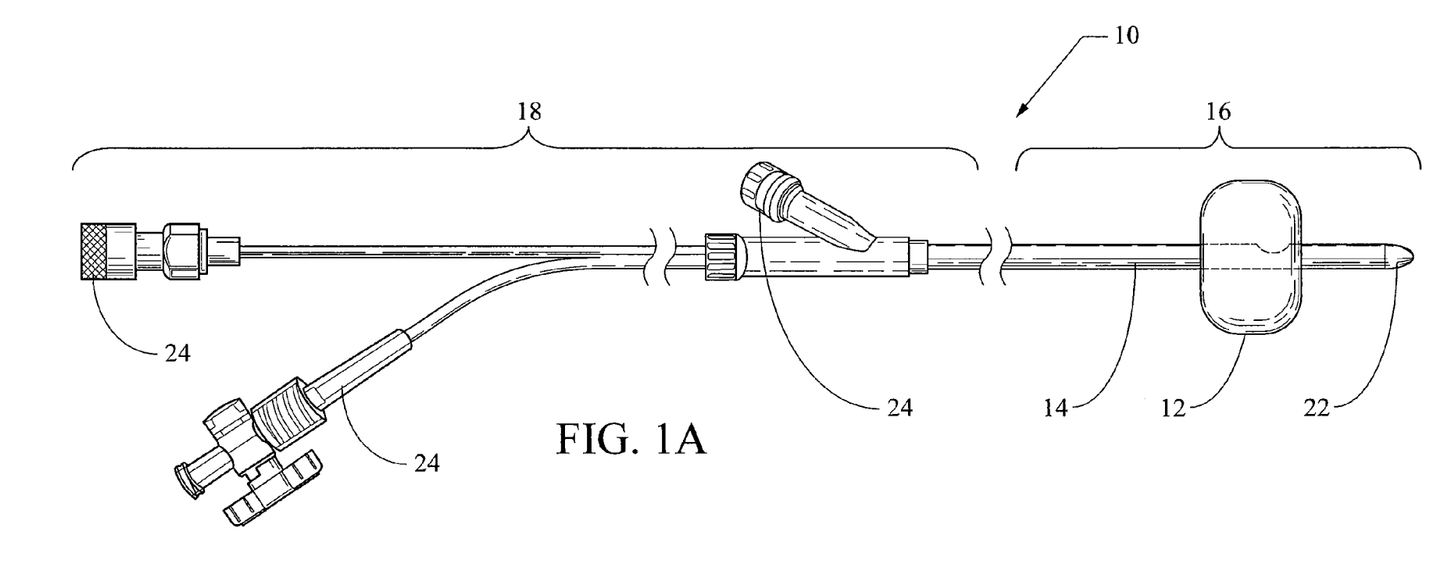
FIG. 1A depicts a device having an elongate member and an inflatable member configured to contain a magnetic agent, in accordance with one embodiment.

Referring to the figures, FIG. 1A depicts a perspective view of one illustrative embodiment. The device 10 comprises an elongate member 14 having a distal portion 16 and a proximal portion 18. At least one lumen extends through the proximal portion and at least partially through the distal portion. The lumen is fluidly interconnected with the interior of at least one inflatable member, such as a balloon 12. Device 10 may include additional lumens extending through the length of the elongate member. Preferably, at least one lumen is configured to allow transit of a wire-guide therethrough. Optionally, however, distal end 22 may be closed. Proximal portion 18 may include one or more proximal couplings 24. Preferably at least one coupling is configured to couple with a device adapted to deliver a magnetic agent to the lumen fluidly interconnected with balloon 12. Additionally, one or more couplings may be configured to couple with a device to remove the magnetic agent from the balloon by way of the lumen fluidly interconnected with the balloon. Alternatively, the proximal portion can include other couplings configured to mate with other devices.

Figure 1B:
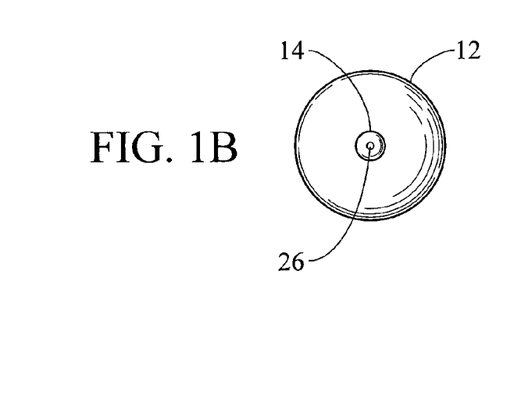
FIG. 1B depicts a distal end view of the device shown in FIG. 1A.

FIG. 1B depicts a distal-end view of elongate member 14 wherein a wire guide lumen 26 extends through the length of the elongate member, and wherein balloon 12 circumscribes an outer diameter of distal portion 16.

Figure 2A:
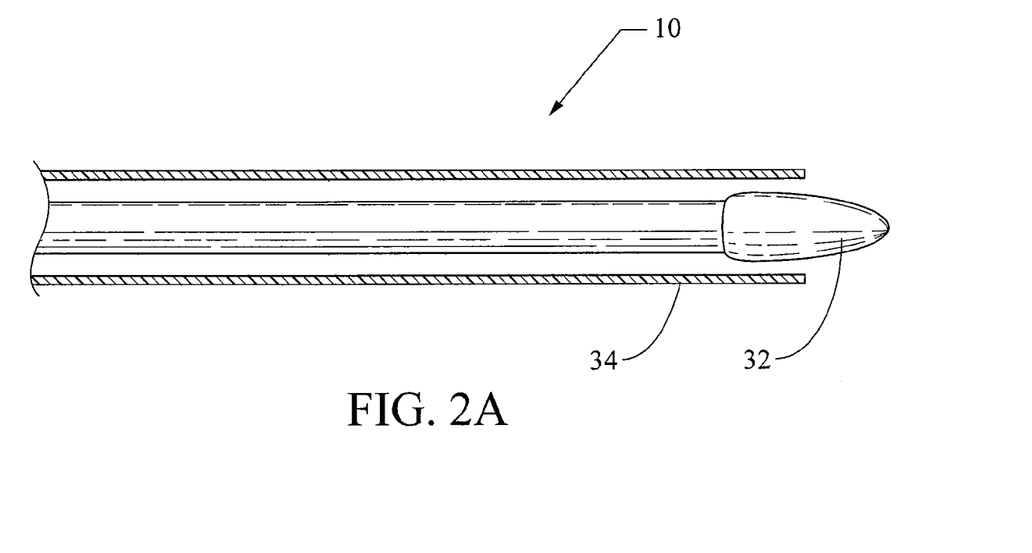
FIG. 2A depicts a device having an elongate member, an inflatable member configured to contain a magnetic agent, and an outer sheath, wherein the device is in a delivery configuration.
Figure 2B:
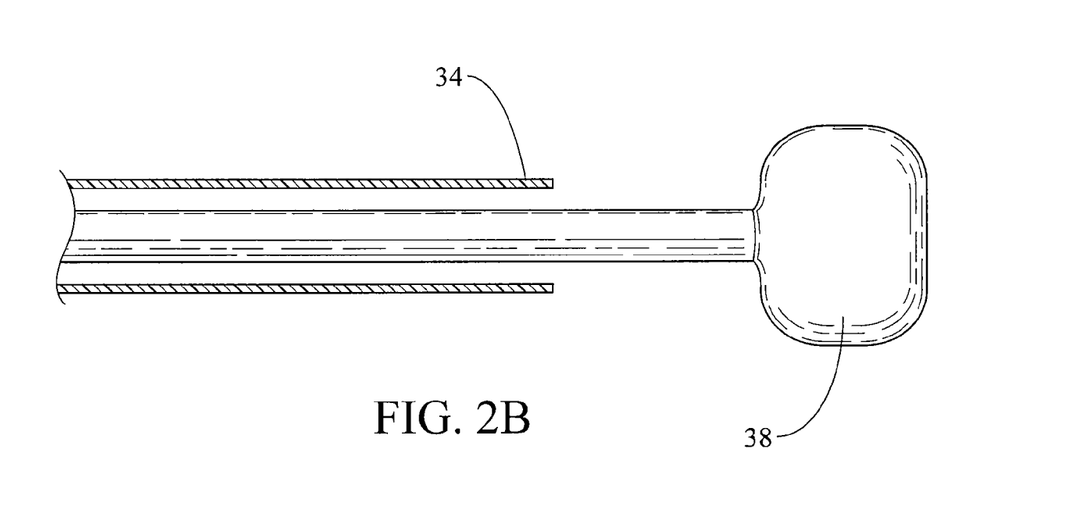
FIG. 2B depicts the device shown in FIG. 2A wherein the device is in a deployed configuration.

In one embodiment, as shown in FIG. 2A, device 10 may include an inflatable balloon 32 disposed on the distal end of the elongate member. The device may further include a sheath 34. The sheath may aid in advancing and accessing a desired location within a patient. The sheath may also protect the balloon and elongate member during advancement. The sheath may comprise any suitable material for the intended use. For example, the sheath may comprise HDPE, PTFE, PEBA, PET, polyolefin, polyurethane, polyimide, nylon, and combinations thereof. Preferably, balloon 32 can be partially inflated as the device is advanced to the desired location. This may provide for a more rounded distal end. Once the device is at the desired location, the protective sheath can be retracted longitudinally towards the proximal portion to expose all or part of the distal portion, including the partially inflated balloon. The balloon can then be inflated to an inflated configuration 38, as shown in FIG. 2B.

Figure 3A:
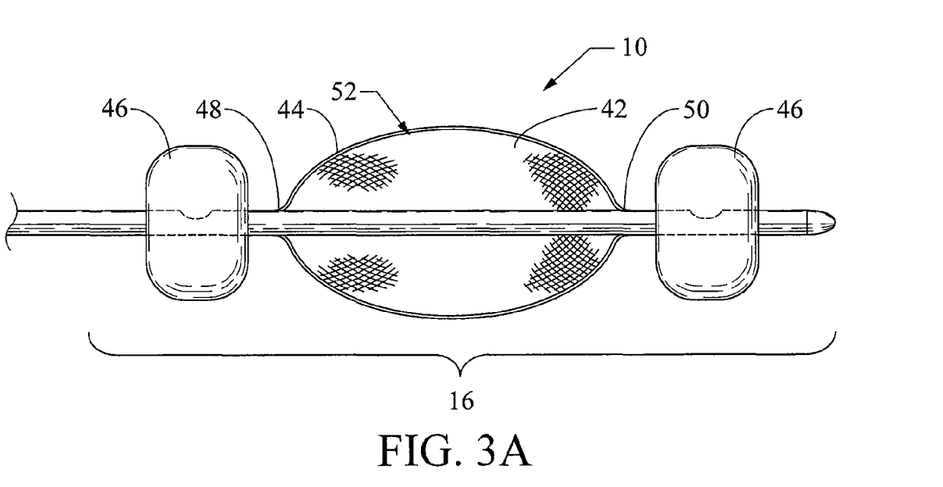
FIG. 3A depicts a device in the deployed configuration, wherein the device comprises a sling and expansion elements.
Figure 3B:
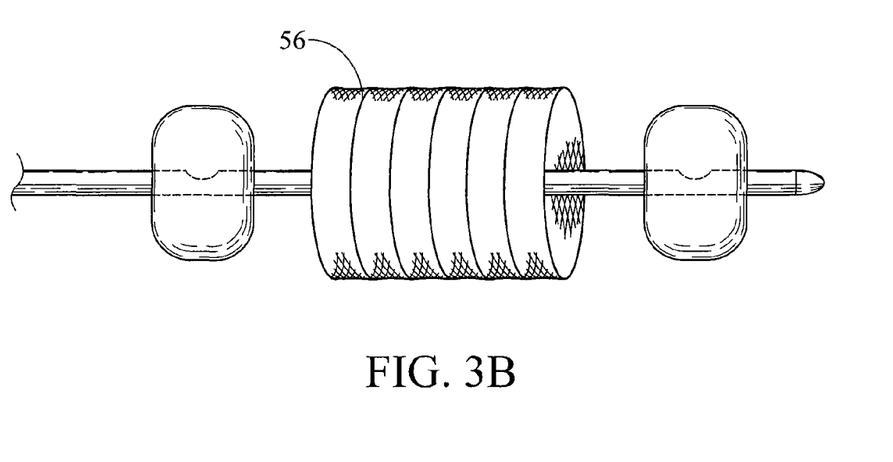
FIG. 3B depicts a device in the deployed configuration, wherein the device comprises a sling and expansion elements.
Figure 3C:
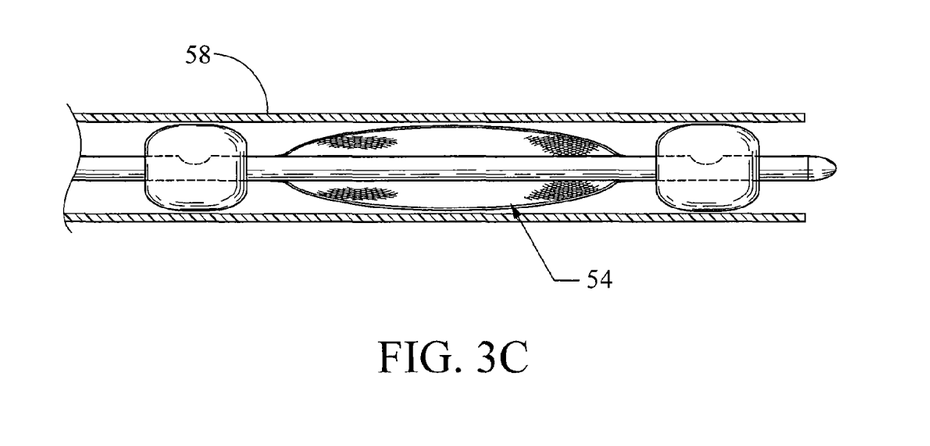
FIG. 3C depicts the device shown in FIG. 3A in a delivery configuration, the device contained by an outer sheath.

FIGS. 3A-3C depict another illustrative embodiment. In this embodiment, device 10 includes a sling 42 disposed on distal portion 16 of the elongate member. The sling may be used to grasp and retract tissue, and may increase the surface area of tissue engaged by the device. By increasing the surface area engaged by the device, the pressure per unit area can be reduced, which may help minimize trauma to the manipulated tissue.

Preferably, the sling is expandable from a delivery configuration to a deployment configuration. For example, in one embodiment, the sling may be wrapped, folded, or compressed into a delivery configuration 54 (FIG. 3C), and thereafter unwrapped, unfolded, or expanded into a deployment configuration 52 (FIG. 3A). The sling may be comprised of an elastic material capable of elastic expansion from a delivery configuration to a deployment configuration. As shown in FIG. 3A, the device can further include one or more expansion elements 44 disposed on distal portion 16 of the elongate member, and can be expanded from a delivery configuration 54 to a deployment configuration 52. The expansion elements may minimize the need for endoscopic/laparoscopic manipulation of the device after deployment. The expansion elements can comprise any material or structure suitable for the intended use. For example, the expansion elements can be wires, threads, strands, or the like. As shown in FIG. 3A, the expansion elements may be fixedly attached to the elongate member at one or more points, such as for example, points 48 and 50. The expansion elements can be fixedly attached to sling 42, such that the expansion elements are configured to expand the sling from a delivery configuration 54 to a deployment configuration 52. In another embodiment shown in FIG. 3B, the expansion elements can be ring structures 56 capable of expansion from a delivery configuration to a deployment configuration. In some embodiments, the expansion elements may be self-expanding. The expansion elements may comprise a superelastic material, such as a superelastic metal alloy (e.g., nitinol). Optionally, the sling material may comprise a superelastic material. In such an embodiment, the expansion elements may be absent because the sling itself may be sufficiently self-expanding.

In FIGS. 3A-3C, the expansion elements and the sling are disposed between two inflatable members, depicted as balloons 46, on the distal portion of the elongate member. This configuration may allow the balloons to engage a less sensitive area with a strong force while the sling engages a more sensitive area with a less strong force. However, other embodiments and configurations are contemplated in accordance with the present disclosure.

Figure 4A:
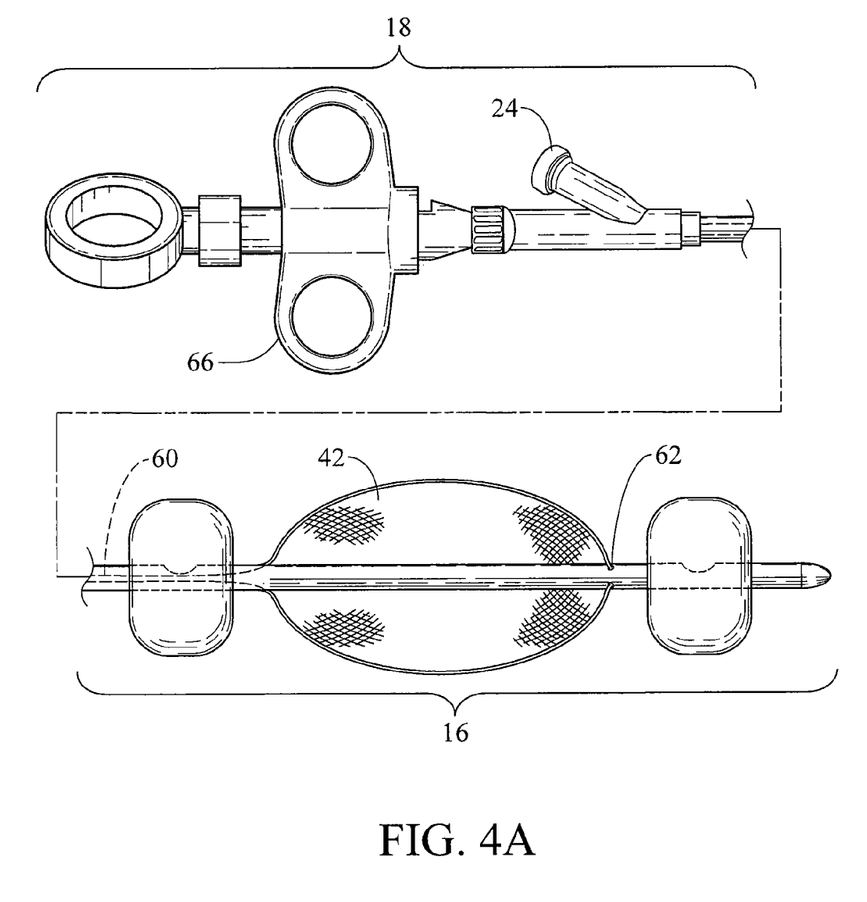
FIG. 4A depicts a device having a mechanically expandable sling.
Figure 4B:
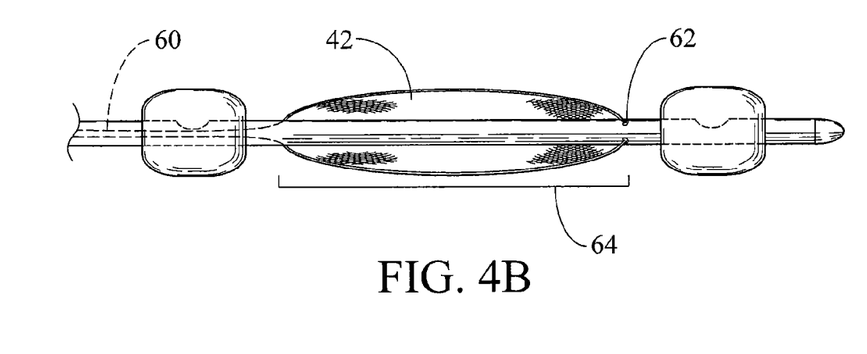
FIG. 4B depicts the device of FIG. 4A wherein the sling is in a delivery configuration.

FIGS. 4A-4B show that the expansion elements may be mechanically expandable. FIG. 4A shows sling 42 in an expanded configuration. FIG. 4B shows the sling in an unexpanded configuration. In this illustrative embodiment, the elongate member comprises at least one lumen, preferably two, extending through proximal portion 18 and at least partially through the distal portion 16, wherein the lumens each contain a wire 60 disposed through the length of the lumen. The wires are operatively connected at the proximal portion of the elongate member to a handle assembly 66. The wires are anchored at distal portion anchor points 62. A segment 64 of the wires is disposed external the elongate member at the distal portion, wherein the wires are exposed in a location proximal in direction relative to the anchor points. With this configuration, the wires can be advanced longitudinally from the proximal portion toward the distal portion, causing exposed segment 64 to radially extend from the elongate member. Because sling 42 is fixedly attached to exposed segment 64, the sling radially expands upon advancement of the wires toward the distal portion.

Preferably, the devices of the present disclosure can be delivered to, and removed from a site of treatment in a delivery configuration having a minimum diameter. In some embodiments, therefore, the inflatable members are not substantially inflated until reaching a site of treatment. In embodiments including a sling, preferably the sling is radially compressed to a minimum diameter until reaching a site of treatment. In order to compress the devices and aid in transit to a desired location, the devices can be configured to a delivery configuration wherein an outer elongate member 58 (FIG. 3C), for example, contains the device. Once a desired site of treatment is reached, the device can be delivered to the desired location by retracting the outer elongate member, or alternatively, by advancing the device beyond the distal end of the outer elongate member. The device can be expanded to a deployed configuration after retraction or advancement is complete, or alternatively, the device can expand to a deployed configuration simultaneous with retraction of the outer elongate member. In other embodiments, the delivery configuration can be maintained prior to deployment of the device by other suitable devices, including for example, a suture, a tube or other restraining material around all or part of the device.

In another aspect, the present disclosure includes a plurality of inflatable members interconnected by a sling and configured to contain a magnetic agent. In some embodiments, the inflatable members can be adapted for inflation prior to insertion into a patient. In other embodiments, the inflatable members can be adapted for inflation during or after insertion in a patient. The sling is generally intended to engage selected organs and tissue such that the organs and tissue can be retracted while contacting the sling.

Figure 5A:
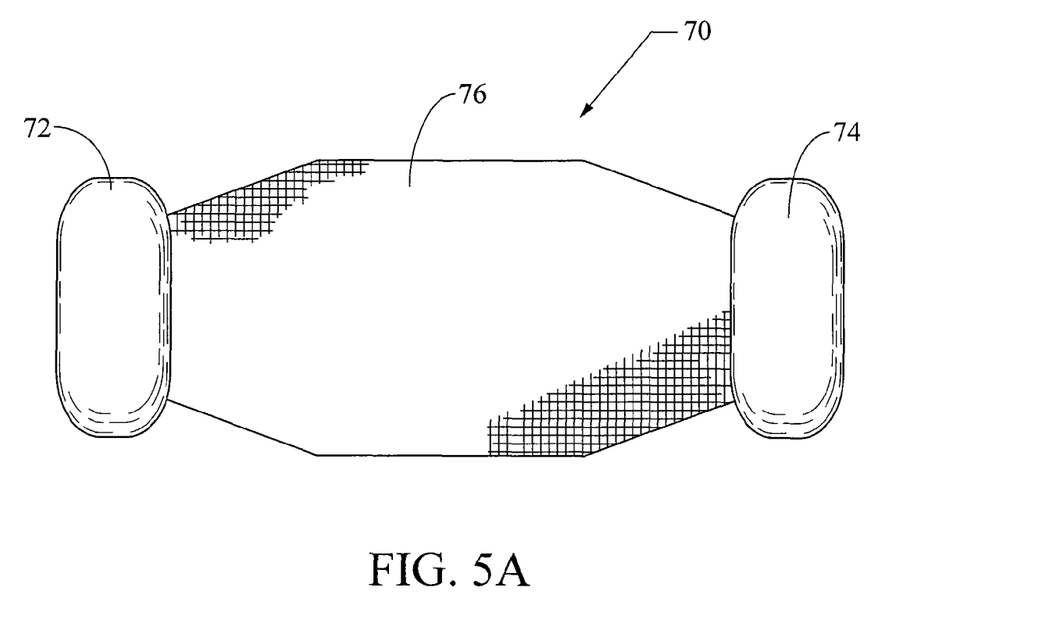
FIG. 5A depicts a device comprising two inflatable members configured to contain a magnetic agent, wherein the inflatable members are connected by a sling.
Figure 5B:
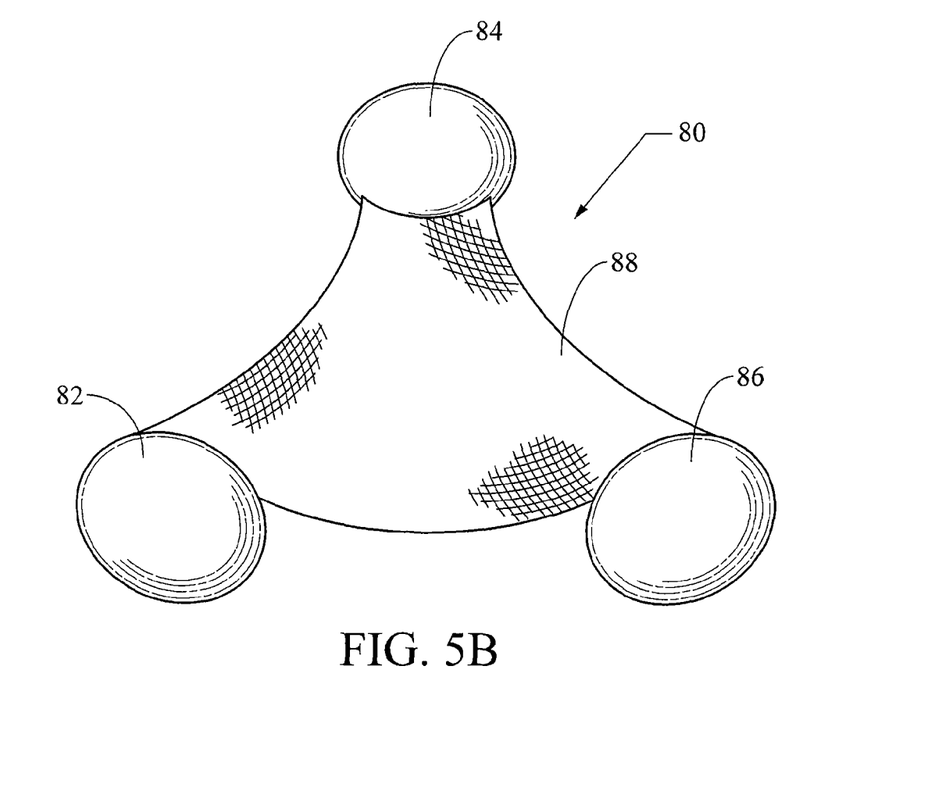
FIG. 5B depicts a device comprising three inflatable members configured to contain a magnetic agent, wherein the inflatable members are connected by a sling.

FIG. 5A depicts a perspective view of one illustrative embodiment. In this embodiment, a device 70 comprises two inflatable members 72 and 74 interconnected by a sling 76. FIG. 5B depicts another illustrative embodiment wherein a device 80 comprises three inflatable members 82, 84, and 86, interconnected by a sling 88. The inflatable members can be adapted to receive a magnetic agent prior to, during or after deployment to a target site. For example, the device may be manufactured having small inflatable members prefilled with magnetic agent. Alternatively, the inflatable members may be inflated immediately prior to use by having a portion adapted to receive an inflation device (e.g., the inflatable members may be self-sealing and adapted to receive a needle). The device may then be introduced through a surgical trocar or endoscope, for example. In another embodiment, the inflatable members may be connected to a detachable tube by a valve that seals when the connection is broken. In this manner, the device may be introduced with a minimum diameter, inflated with magnetic agent, and thereafter disconnected from the inflation lumen. In another embodiment, the inflatable members may include a valve as disclosed in U.S. Application Ser. No. 61/286,661 entitled, "Low-Profile One-Way Valve", which is hereby incorporated by reference in its entirety. The inflatable members can be configured to the same size, or alternatively, different sizes and shapes in accordance with the surgical procedure. In addition, the inflatable members can be adapted to different thicknesses and internal volumes. The sling can be configured to any appropriate size, adapted to cover any appropriate surface area for the intended use. Other embodiments can have any suitable number of inflatable members interconnected by the sling. The inflatable members can be connected to the sling by any suitable method. For example, the inflatable members may be attached by mechanically attaching the sling to the inflatable members with, for example, suturing. Alternatively, the inflatable members may be attached by appropriate thermal or chemical treatment of the inflatable members and the sling. Alternatively, the inflatable members may be integral with the sling. For example, the inflatable members may be fabricated by folding over a selected portion of the sling material and thereafter sealing the edges. The integral inflatable members can be inflated prior to, during, or after deployment.

Figure 6:
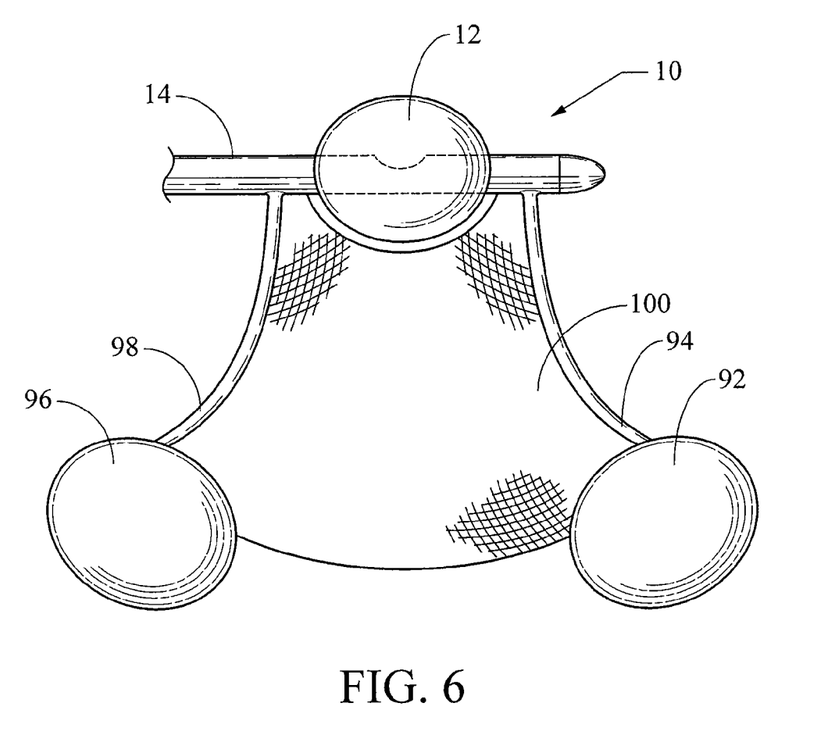
FIG. 6 depicts a device comprising three inflatable members configured to contain a magnetic agent, wherein the inflatable members are connected by a sling.

FIG. 6 depicts another illustrative embodiment. In this embodiment, device 10 may include one or more inflatable members, such as balloon 92, interconnected by a sling 100 to a distal portion of the elongate member 14 or with balloon 12. In some embodiments, balloon 92 may be fluidly interconnected with a lumen 94 disposed through the proximal portion and at least partially through the distal portion of the elongate member 14, and partially disposed external the elongate member along an edge of the sling leading to the balloon 92. In the particular embodiment illustrated, the device includes a third balloon 96. Similar to balloon 92, balloon 96 may be fluidly interconnected with a lumen 98 partially disposed external the elongate member along an edge of the sling leading to balloon 96.

Figure 7:
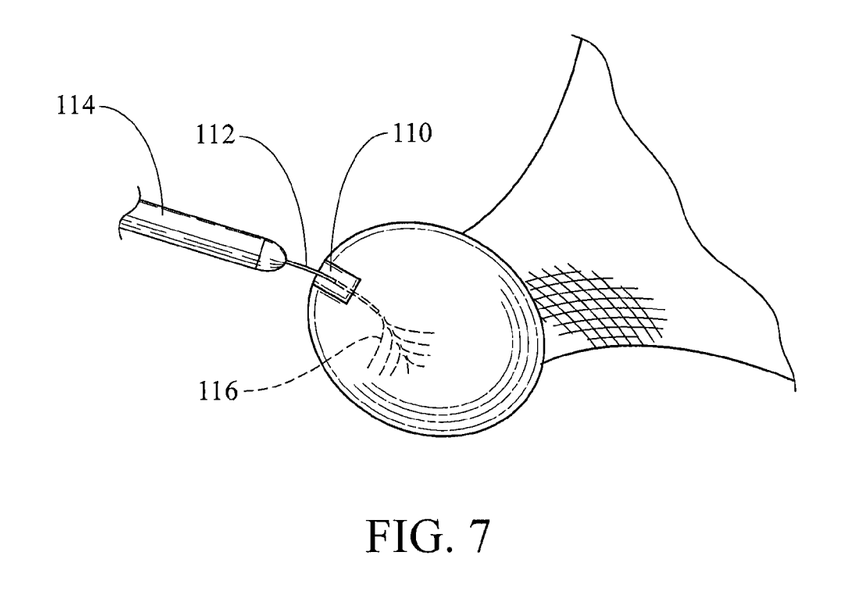
FIG. 7 depicts an inflatable member comprising a valve system adapted to receive an inflation device.

FIG. 7 depicts another illustrative embodiment wherein the inflatable members can include one or more ports or valves 110 adapted to receive a needle 112 or other device configured to inject magnetic agent therein. For example, the valve or port can be configured to receive a pump needle similar in design to a conventional basketball pump, but wherein the pump needle is adapted for introduction into a patient during a minimally invasive surgical procedure. In some embodiments, the inflatable members may comprise an elastomeric material configured to reseal after being penetrated by an inflation instrument. The inflatable members may comprise the elastomeric material in selected area of the member wall, at a port or valve for example, or the elastomeric material may be distributed throughout the inflatable member material. Self-sealing elastomeric membrane materials include for example, polydimethylsiloxane, polyurethane, hydrogel, PET and others. With this approach, the inflatable members can be deployed in a fully deflated or partially deflated configuration. Once deployed at a desired location, the inflatable members can be inflated by mating with a needle or other inflating device 114, wherein the inflating device will deliver a magnetic agent 116. These embodiments may allow inflatable members of the present disclosure to be introduced in a delivery configuration and later inflated to a deployment configuration without the need for permanent attachment of the inflatable members to an inflation lumen. Similarly, the inflatable members may be deflated or partially deflated by mating with a needle or other deflation device configured to remove the magnetic agent, thus allowing the inflatable members to be removed in a deflated or partially deflated configuration. Optionally, the valve may be configured to mate with a detachable lumen wherein the valve seals upon detachment from the lumen.

In another embodiment, where the inflatable members comprise a non-self sealing material in a selected portion of the member wall, or alternatively, throughout the member material, the inflatable members may be deflated by puncturing the member with a needle or other device and allowing the magnetic agent to escape and dissipate into the patient, wherein the magnetic agent is a biocompatible material adapted for release into a patient. This approach may allow the inflatable members to be removed in a deflated or partially deflated configuration without the need for retraction of the magnetic agent through a lumen, needle, or other device.

With regard to FIGS. 1-7, and other embodiments contemplated by the present disclosure, the one or more inflatable members can comprise compliant materials, semi-compliant materials, non-compliant materials, and combinations thereof. The inflatable members may be inflatable balloons adapted for use within a patient. The inflatable members may be integral with a sling, and optionally, formed from the sling material. The inflatable members can comprise, for example, polyamines, silicone, nylon, latex, natural rubber, synthetic rubber, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LPDE), acrylonitrile polymers and copolymers, acrylonitrile blends, ionomer resins, polyethylene terephthalates, polyacrylenesulfide, and copolyesters. Preferably, the inflatable members comprise compliant or flexible materials, such as for example, latex. Other suitable materials and combinations may also be used in accordance with the intended use.

The inflatable members can have a cross section that is cylindrical, oval, square, rectangular, or other suitable shape. The inflatable members can be configured to receive and contain a magnetic agent. The inflatable members can be configured to hold any suitable volume of magnetic agent in accordance with the surgical procedure the device is being used for. In accordance with the surgical procedure, the inflatable members may be fully inflated, or alternatively, partially inflated. The inflatable members may have any wall thickness suitable for the intended use. Typically, inflatable members adapted for use in medical devices have a wall thickness in the range of 0.030 inches to 0.0005 inches. Inflatable members for other types of medical devices, including balloons, may be suitable for use in accordance with the present disclosure. For example, balloons designed for balloon catheters for temporarily occluding a body vessel to facilitate the injection of contrast agent or for sweeping debris therefrom may be suitable.

The magnetic agent of the present disclosure can be comprised of any suitable magnetic substance. In some embodiments, the magnetic agent comprises a ferrofluid, which is a stable colloidal suspension of sub-domain magnetic nanoparticles in a liquid carrier. In other embodiments, the magnetic agent comprises a magnetorheological fluid, which is a suspension of micrometer sized magnetic particles in a liquid carrier. The liquid carrier may be any liquid carrier suitable for the intended use. For example, the liquid carrier may comprise water, water-alcohol mixtures, or hydrocarbons such as paraffin oil or synthetic esters. The magnet particles may comprise, for example, cobalt ferrite, magnetite, or hematite. The magnetic particles may be coated with a suitable surfactant, such as for example, citric acid, oleic acid, or other surfactants suitable for the intended use. Biocompatible magnetic agents are commercially available, for example, from Ferrotec (USA) Corporation of Bedford, N.H. A biocompatible magnet agent may be prepared, for example, by placing a ferromagnetic material such as stainless steel (400-series) in a viscous carrier such as vegetable oil.

The magnetic device of the present disclosure can comprise any suitable material or device for generating a magnetic field capable of manipulating a balloon containing a magnetic agent wherein the balloon is disposed in a patient. In general, when the selected magnetic field is applied, the particles in the magnetic agent align with the magnetic flux. Preferably, manipulating the inflatable member with the magnetic device causes movement or retraction of the target tissue or target organ. The magnetic device may be external to the patient during manipulation of the inflatable member and the target tissue or target organ. In one embodiment, the magnetic device can be a permanent magnet. For example, the magnetic device may be a neodymium based magnet, a samarium-cobalt based magnet, or an alnico based magnet. In another embodiment, the magnetic device can be an electromagnet. For example, the magnetic device can be an electromagnet comprising a copper wire surrounding an iron based core. Because the field strength of an electromagnet is adjustable with the current applied, an electromagnet may be preferred in procedures demanding a magnetic field of variable field strength. Those skilled in the art will appreciate that other magnetic devices may be used as appropriate. The magnetic device may be tailored to any size or shape suitable for the intended use. For example, the magnetic device may be cylindrical, elliptical, or another suitable shape.

The sling of the present disclosure is generally intended to be a flexible and atraumatic material. The sling may be fabricated from, for example, a fabric or mesh material. The sling can be comprised of any of a variety of suitable synthetic or naturally occurring biocompatible materials, biocompatible metals, and combinations thereof. Such materials, for example, may be filamentous or non-filamentous, elastic or inelastic, and may be porous, microporous, perforated, or impermeable. The properties of the sling may be selected as appropriate based on the surgical procedure used to deploy the device and the application for which the device is used. Biocompatible metals include, for example, stainless steel, gold, silver, tantalum, titanium, and shape memory alloys such as nitinol. Synthetic materials include, for example, polyester, polyurethane, polyamide, polytetrafluoroethylene (PTFE), polytetrafluoroethylene (EPTFE), polyethylene terephthalates, silicone, and nylon. Naturally occurring biocompatible materials include, for example, cadaveric or animal tissue such as fascia lata, rectus fascia and processed collagen. In addition to the above, the sling material may comprise a biocompatible magnetic material. The magnetic material may be dispersed evenly throughout the sling, or may have higher concentrations of magnetic material in certain portions thereof.

In accordance with the type of surgical procedure for which the device is being used, in some embodiments the sling material may comprise an elastic material, such as for example, knitted polyester. In other embodiments, the sling may comprise an inelastic or minimally elastic material, such as for example, woven polyester. In other embodiments, the sling may comprise a superelastic material.

Methods of Treatment

One aspect of the present disclosure provides a method for manipulating tissue and organs. Such a method can be of use in the retraction of organs and tissue during minimally invasive surgery. The method can be of particular use in retraction of organs during endoscopic or laparoscopic surgery.

Figure 8:
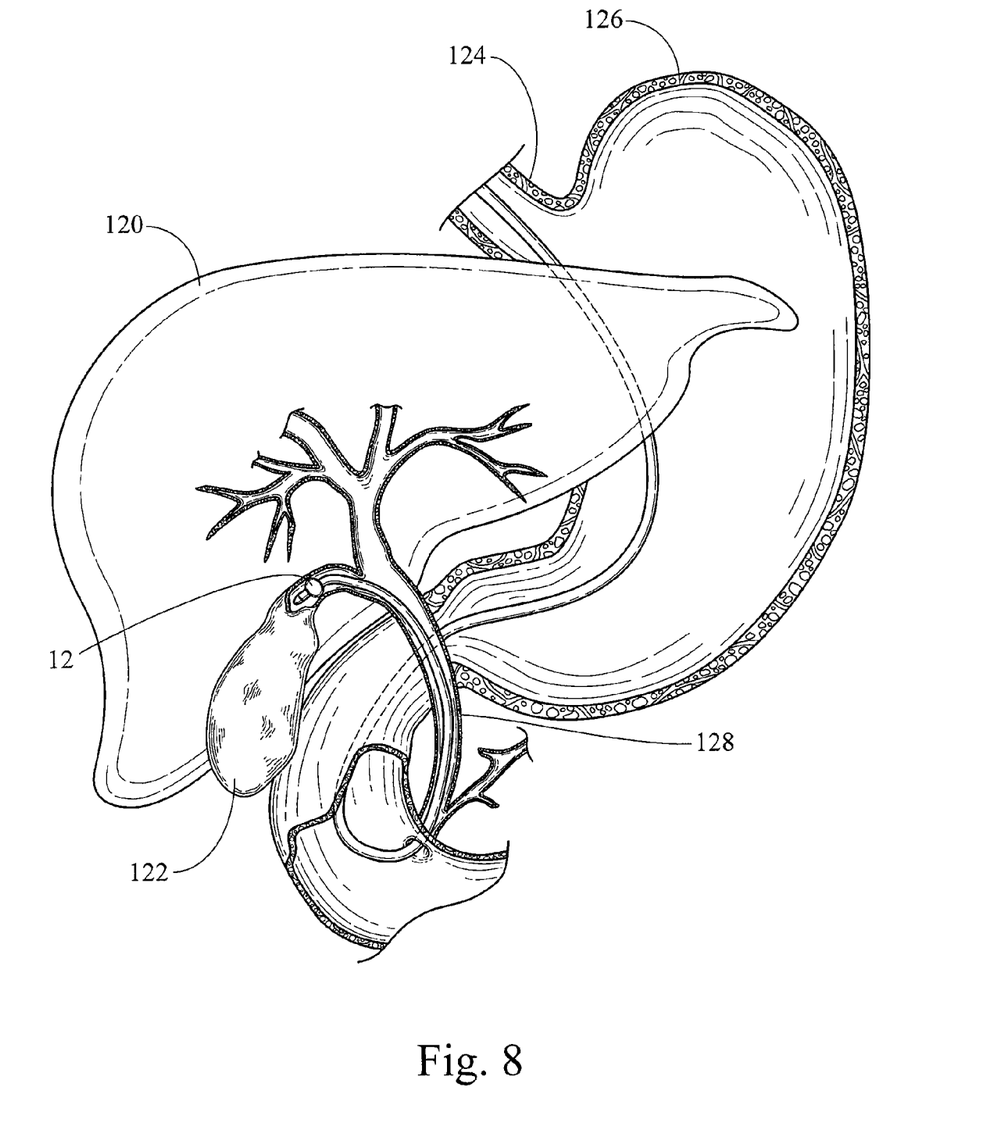
FIG. 8 depicts one embodiment of the present disclosure wherein the device is deployed in a gall bladder and can be used to retract the gall bladder and liver.

In one exemplary embodiment, as shown in FIG. 8, device 10 can be used to retract, for example, the liver 120. Because the gall bladder 122 is attached to the liver, if the gall bladder is retracted, the liver will also be retracted. For some procedures, it is advantageous to retract the liver. Endoscopic Retrograde Cholangiopancreatography (ERCP) may be used to access the gall bladder. ERCP involves inserting an endoscope into a patient's mouth and through the esophagus 124, stomach 126, and duodenum until it reaches the area where the ducts of the biliary tree and the pancreas open into the duodenum. The endoscope can then used to view the liver, gall bladder, bile ducts, and pancreas. Dyes may be injected through the endoscope and into the organs in order to aid in visualization. In this exemplary embodiment, a wire guide is placed in the gall bladder by ERCP through the bile duct 128. A device of the present disclosure, such as the device of FIGS. 1A-1B, comprising an elongate member 14 can then be advanced over the wire guide into the gall bladder. Next, the wire guide can be removed from the gall bladder, leaving distal portion 16 of device 10 in place. A syringe can be attached to a proximal coupling 24 of the device and used to inject magnetic agent into balloon 12. To manipulate the liver, for example, a magnetic device on the outside of the patient's body may first be placed near the gall bladder. Once the magnetic field created by the magnetic device associates with the magnetic agent filled balloon wherein the balloon moves in response to movement of the magnetic device, the liver can be retracted by dragging the magnetic device in a desired direction. This exemplary procedure may be applied in a similar manner to other organs and tissue. In this respect, organs and tissue can be retracted in any desired direction. Once the organ is retracted, the liver in this example, there will be a gap created in the space formerly occupied by the organ, thus creating additional space in which to perform surgical procedures. Once the surgical procedure(s) is complete, the magnetic device external to the patient's body can be pulled away or deactivated and the organs and tissue will return to the normal position by force of gravity as well as the organs' other attachments. The balloon can be deflated by pulling the magnetic agent out of the balloon with a syringe attached to a proximal coupling. With the balloon deflated, the device can be pulled out of the gall bladder and out of the patient's body.

Figure 9:
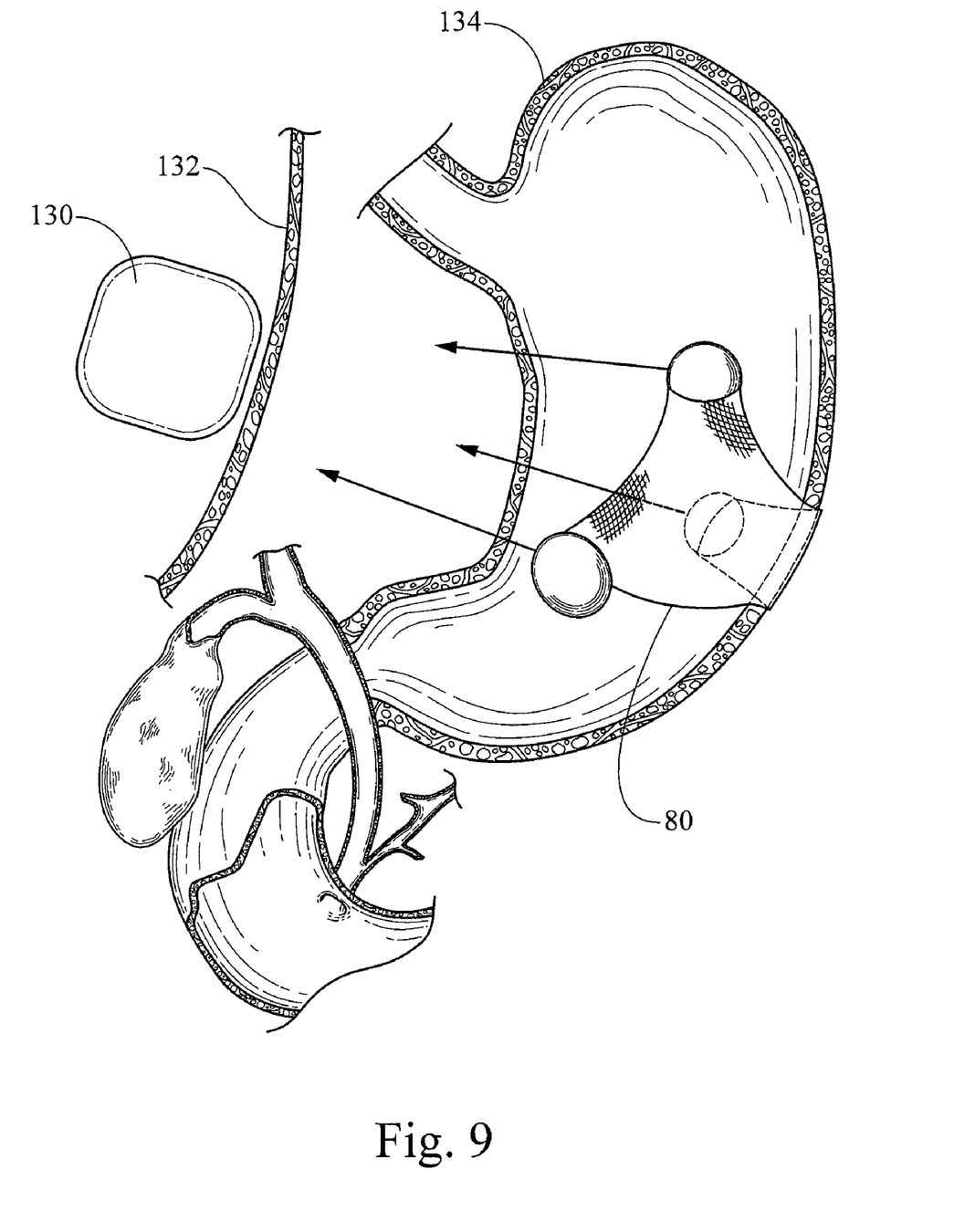
FIG. 9 depicts one embodiment of the present disclosure wherein the device is deployed in a transluminal space and can be used to retract the stomach.

In another exemplary embodiment shown in FIG. 9, device 80 can be used to retract organs and tissue, such as for example, the stomach or a large section of small bowel. In this instance, the inflatable members could be pre-inflated with magnetic agent. Alternatively, the inflatable members could be inflated after introduction using the port/valve system as illustrated in FIG. 7. The device may be introduced using a NOTES procedure (Natural Orifice Translumenal Endoscopic Surgery), for example. In a NOTES procedure, an endoscope is introduced through a natural orifice into a natural luminal space. The endoscope is then placed at a desired location on the wall of the natural lumen and is then subsequently used to make a small incision through the wall of the lumen. The endoscope can then be placed in the transluminal space and used to view the space and perform procedures therein. In this exemplary embodiment, the device 80 could be introduced into the patient and the transluminal space by placing it through an over tube, for example. In this instance, the transluminal space would be that of either the stomach or the small bowel. After introduction, using currently available graspers, the device can be manipulated to capture the desired tissue. Once placed at a desired location, one or more magnetic devices, represented schematically as 130, could be applied at an external surface 132 of the patient's body. Preferably, the inflatable members can be pulled towards a less delicate area such as the body wall while the sling may be used to more gently retract the organ(s) and tissue, the stomach 134 in this illustration. With this approach, a large section of small bowel or stomach can be retracted in the sling. Once the procedure is complete, the magnetic device can be removed or discontinued, thereby discontinuing retraction of the selected organ(s) and tissue. Using currently available graspers, the device 80 can be retrieved and thereafter removed through the endoscope working channel, or alternatively, another device having a lumen of sufficient diameter to accommodate device 80. In some procedures, it may be possible to retrieve the device without extraction through a working channel or lumen. For example, in some procedures, the device may be grasped and extracted through an incision or other point of entry into the patient. Since the inflatable members are generally made of compliant materials, the members can stretch as they are pulled through the sites of entry. Alternatively, the magnetic agent can be removed from the inflatable members through a port or valve system, through a self-sealing approach as presently disclosed, or in some embodiments, by puncturing the inflatable members and allowing the magnetic agent to dissipate into the patient's body. After the inflatable members are fully or partially deflated, the device can be removed with currently available graspers or the like, optionally through the endoscope or another device having an appropriately sized lumen.

While various embodiments have been described, it will be apparent to those of ordinary skill in the art that many more embodiments and implementations are possible within the scope of the invention. Accordingly, the invention is not to be restricted except in light of the attached claims and their equivalents.

The invention claimed is:

1. A system for manipulating tissue, comprising:
a magnetic agent;
an inflatable member configured to contain the magnetic agent;
a magnetic device configured to manipulate the position of the inflatable member containing the magnetic agent, wherein the inflatable member containing the magnetic agent is configured to manipulate the position of a tissue in response to a magnetic field emitted by the magnetic device;
an elongate member comprising a proximal portion, a distal portion, and a lumen disposed through the proximal portion and at least partially through the distal portion, the lumen fluidly interconnected with the inflatable member;
a sling disposed on the distal portion of the elongate member, the sling having a flexible planar surface configured to engage the tissue; and
an expansion element connected to the sling, wherein the expansion element is adapted to radially expand the sling from a compressed nonexpanded configuration to an expanded configuration.

2. The system of claim 1 wherein the elongate member further comprises a second lumen disposed through the proximal portion and the distal portion, the second lumen configured to receive a wire guide therethrough.

3. The system of claim 1, further comprising a sheath adapted to contain the elongate member.

4. The system of claim 1 wherein the expansion element comprises a superelastic material.

5. The system of claim 1 wherein the expansion element comprises a wire anchored at the distal portion and operatively connected at the proximal portion, the wire having a segment disposed external the elongate member at the distal portion, wherein the sling is connected to the segment of wire disposed external the elongate member, wherein the wire can be advanced longitudinally toward the distal portion, and wherein the sling radially expands upon advancement of the wire toward the distal portion.

6. The system of claim 1 wherein the sling comprises a magnetic agent.

7. The system of claim 1 wherein the sling comprises a superelastic material.

8. The system of claim 1 wherein the sling is connected to a second inflatable member configured to contain the magnetic agent, the second inflatable member being connected to the sling at a location spaced apart from the elongate member.

9. A system for manipulating tissue, comprising:
a magnetic agent;
an inflatable member configured to contain the magnetic agent;
a magnetic device configured to manipulate the position of the inflatable member containing the magnetic agent, wherein the inflatable member containing the magnetic agent is configured to manipulate the position of a tissue in response to a magnetic field emitted by the magnetic device;
an elongate member comprising a proximal portion, a distal portion, and a lumen disposed through the proximal portion and at least partially through the distal portion, the lumen fluidly interconnected with the inflatable member;
a sling disposed on the distal portion of the elongate member; and
an expansion element connected to the sling, wherein the expansion element is adapted to radially expand the sling, wherein the expansion element comprises a wire anchored at the distal portion and operatively connected at the proximal portion, the wire having a segment disposed external the elongate member at the distal portion, wherein the sling is connected to the segment of wire disposed external the elongate member, wherein the wire can be advanced longitudinally toward the distal portion, and wherein the sling radially expands upon advancement of the wire toward the distal portion.

10. The system of claim 9 wherein the elongate member further comprises a second lumen disposed through the proximal portion and the distal portion, the second lumen configured to receive a wire guide therethrough.

11. The system of claim 9 wherein the expansion element comprises a superelastic material.

12. A system for manipulating tissue, comprising:
a magnetic agent;
an inflatable member configured to contain the magnetic agent;
a magnetic device configured to manipulate the position of the inflatable member containing the magnetic agent, wherein the inflatable member containing the magnetic agent is configured to manipulate the position of a tissue in response to a magnetic field emitted by the magnetic device;
an elongate member comprising a proximal portion, a distal portion, and a lumen disposed through the proximal portion and at least partially through the distal portion, the lumen fluidly interconnected with the inflatable member;
a sling disposed on the distal portion of the elongate member, the sling having a flexible planar surface configured to engage the tissue, wherein the sling is connected to a second inflatable member configured to contain the magnetic agent, the second inflatable member being connected to the sling at a location spaced apart from the elongate member.

* * * * *